(12) United States Patent
Nagata et al.

(10) Patent No.: US 10,598,628 B2
(45) Date of Patent: Mar. 24, 2020

(54) GAS SENSOR AND METHOD OF MANUFACTURING THE SAME

(71) Applicant: NGK Spark Plug Co., LTD., Nagoya (JP)

(72) Inventors: Shogo Nagata, Komaki (JP); Takehiro Oba, Konan (JP); Shunya Mihara, Komaki (JP); Kenji Masuda, Komaki (JP)

(73) Assignee: NGK Spark Plug Co., LTD., Nagoya (JP)

( * ) Notice: Subject to any disclaimer, the term of this patent is extended or adjusted under 35 U.S.C. 154(b) by 307 days.

(21) Appl. No.: 15/637,770

(22) Filed: Jun. 29, 2017

(65) Prior Publication Data

US 2018/0003669 A1    Jan. 4, 2018

(30) Foreign Application Priority Data

Jun. 30, 2016  (JP) ................................ 2016-129692
Feb. 14, 2017  (JP) ................................ 2017-024711

(51) Int. Cl.
*G01N 27/407*   (2006.01)
*G01N 27/30*    (2006.01)
*C01B 21/20*    (2006.01)
*G01N 27/22*    (2006.01)

(52) U.S. Cl.
CPC ....... *G01N 27/4073* (2013.01); *G01N 27/304* (2013.01); *G01N 27/4077* (2013.01); *C01B 21/20* (2013.01); *G01N 2027/222* (2013.01)

(58) Field of Classification Search
CPC ....................... G01N 27/4077; G01N 27/4073

USPC ....................................................... 73/23.31
See application file for complete search history.

(56) References Cited

U.S. PATENT DOCUMENTS

| | | | | |
|---|---|---|---|---|
| 7,424,819 B2* | 9/2008 | Fujita | ................. | G01N 27/4071 204/424 |
| 7,461,538 B2* | 12/2008 | Matsuo | .............. | G01N 27/4062 204/424 |
| 7,524,407 B2* | 4/2009 | Hirasawa | ............. | G01N 27/407 204/421 |
| 8,156,790 B2* | 4/2012 | Matsuo | .............. | G01N 27/4062 204/424 |

(Continued)

FOREIGN PATENT DOCUMENTS

JP    2012-230076 A    11/2012
JP    2013181769 A  *  9/2013

*Primary Examiner* — John Fitzgerald
(74) *Attorney, Agent, or Firm* — Leason Ellis LLP

(57) ABSTRACT

A gas sensor includes a sensor element having electrode pads, metal terminal members connected to the respective electrode pads, separators, and lead wires connected to the rear ends of the metal terminal members. Each metal terminal member has a forward locking portion and a rear locking portion provided at the forward and rear ends, respectively. The separator is composed of a forward separator and a rear separator connected to each other. The forward separator includes a first locking portion having a rearward-facing surface, and the rear separator includes a second locking portion having a forward-facing surface. The metal terminal member is held between the forward separator and the rear separator in a state in which the forward locking portion is in locking engagement with the rearward-facing surface and the rear locking portion is in locking engagement with the forward-facing surface.

6 Claims, 14 Drawing Sheets

(56) References Cited

U.S. PATENT DOCUMENTS

| | | | |
|---|---|---|---|
| 8,191,414 B2* | 6/2012 | Kume | G01N 27/4062 |
| | | | 73/114.73 |
| 9,151,728 B2* | 10/2015 | Kato | G01N 27/4062 |
| 9,482,637 B2* | 11/2016 | Oba | G01N 27/407 |
| 10,031,047 B2* | 7/2018 | Oba | G01M 15/104 |
| 10,203,301 B2* | 2/2019 | Mihara | G01N 27/4162 |
| 2002/0017127 A1* | 2/2002 | Nakano | G01N 27/4062 |
| | | | 73/31.05 |
| 2005/0040039 A1* | 2/2005 | Kojima | G01N 27/4071 |
| | | | 204/424 |
| 2008/0295576 A1* | 12/2008 | Yamauchi | G01N 27/4067 |
| | | | 73/23.31 |
| 2009/0126456 A1* | 5/2009 | Matsuo | G01N 27/4062 |
| | | | 73/23.31 |
| 2009/0223818 A1* | 9/2009 | Matsui | G01N 27/4062 |
| | | | 204/412 |
| 2010/0139364 A1* | 6/2010 | Kume | G01N 27/4077 |
| | | | 73/23.31 |
| 2010/0139379 A1* | 6/2010 | Kume | G01N 27/4062 |
| | | | 73/114.73 |
| 2014/0224044 A1* | 8/2014 | Oba | G01N 33/0009 |
| | | | 73/866.5 |
| 2014/0298931 A1* | 10/2014 | Oba | G01N 27/4062 |
| | | | 73/866.5 |
| 2016/0209351 A1* | 7/2016 | Oba | G01N 27/4062 |
| 2017/0307478 A1* | 10/2017 | Oba | G01N 27/4062 |
| 2017/0307560 A1* | 10/2017 | Oba | G01N 27/304 |
| 2017/0370877 A1* | 12/2017 | Mihara | G01N 27/4162 |
| 2018/0011047 A1* | 1/2018 | Oba | G01N 27/4062 |
| 2018/0011048 A1* | 1/2018 | Oba | G01N 27/4062 |
| 2018/0011049 A1* | 1/2018 | Oba | G01N 27/4062 |

* cited by examiner

GAS SENSOR AND METHOD OF MANUFACTURING THE SAME

This application claims the benefit of Japanese Patent Applications No. 2016-129692, filed Jun. 30, 2016 and No. 2017-024711, filed Feb. 14, 2017, all of which are incorporated herein in their entireties by reference.

FIELD OF THE INVENTION

The present invention relates to a gas sensor having a sensor element for detecting the concentration of a particular gas to be detected, and to a method of manufacturing the same.

BACKGROUND OF THE INVENTION

A known gas sensor for detecting the concentration of oxygen or NOx in exhaust gas of an automobile or the like has a plate-like sensor element which uses solid electrolyte.

In a widely used gas sensor of such a type, a plurality of electrode pads are provided on the outer surface of a rear end portion of the plate-like sensor element, and metal terminal members are brought into electrical contact with the electrode pads so as to output a sensor output signal from the sensor element and supply electricity to a heater stacked on the sensor element (Japanese Patent Application Laid-Open (kokai) No. 2012-230076 (FIGS. 3 and 4)).

As shown in FIG. 14, each metal terminal member 200 is formed from a metal plate through, for example, cutting and raising, and has a strip-like shape. The metal terminal member 200 has a folded-back portion 202 whose distal end portion is folded back toward a sensor element (not shown) for elastic contact with an electrode pad of the sensor element, and a crimp portion 204 to which a distal end of a lead wire 146 is fixed by means of crimping.

The metal terminal member 200 also has a locking portion 206 which protrudes in a direction opposite the folded-back portion 202 thereof and has an L-shaped cross section. The locking portion 206 is accommodated in an L-shaped groove 300g formed on the forward side of a separator hole 300h of a separator 300. The locking portion 206 comes into locking engagement with a forward-facing surface 300s of the groove 300g, whereby the metal terminal member 200 is held in the separator 300.

Notably, in the example of FIG. 14, the metal terminal member 200 is rotated counterclockwise by about 90 degrees, and the locking portion 206 is inserted into the upper right groove 300g. A total of four such metal terminal members 200 are individually accommodated in different grooves 300g.

The lead wire 146 is connected (crimped) to the metal terminal member 200 as follows. First, the lead wire 146 is inserted into the separator hole 300h of the separator 300 from the rear side of the separator 300 and is pulled out toward the forward F side of the separator 300. Next, a distal end portion of the lead wire 146 is fixed, by means of crimping, to the crimp portion 204 of the metal terminal member 200 disposed on the forward side of the separator 300, whereby the lead wire 146 is connected to the metal terminal member 200.

Then, when the lead wire 146 is pulled toward the rear R side such that the lead wire 146 is pulled out rearward of the separator 300, the metal terminal member 200 connected to the lead wire 146 is also pulled toward the rear R side. As a result, the locking portion 206 is accommodated in the groove 300g and comes into locking engagement with the forward-facing surface 300s of the groove 300g, thereby preventing rearward coming off of the metal terminal member 200. In this manner, the metal terminal member 200 is incorporated into the separator 300.

Problem to be Solved by the Invention

However, in the case of the conventional metal terminal member 200, the locking portion 206 prevents only rearward coming off of the metal terminal member 200. Therefore, when an external force or the like acts on the metal terminal member 200, the metal terminal member 200 may move forward and the electrical connection between the metal terminal member 200 and the corresponding electrode pad may become unstable. Also, in the case where the resistance against coming off is increased by decreasing the clearance between the locking portion 206 and the wall surface of the groove 300g, when the metal terminal member 200 is incorporated into the separator 300, a larger frictional force is produced between the locking portion 206 and the wall surface of the groove 300g. In such a case, the lead wire 146 receives larger pulling-in load toward the rear R side, whereby the efficiency of assembling work decreases.

Thus, an object of the present invention is to provide a gas sensor which can reliably hold metal terminal members within a separator and realizes stable electrical connection between the metal terminal members and electrode pads of a sensor element. Another object of the present invention is to provide a method of manufacturing such a gas sensor.

SUMMARY OF THE INVENTION

Means for Solving the Problem

In order to solve the above problem, a gas sensor of the present invention comprises a sensor element having a plate shape, extending in a direction of an axial line and having an electrode pad on an outer surface of a rear end portion thereof; a metal terminal member extending in the direction of the axial line and electrically connected to the electrode pad; a tubular separator which holds the metal terminal member and surrounds the rear end portion of the sensor element; and a lead wire connected to a rear end portion of the metal terminal member and extending rearward of the separator, wherein the metal terminal member has a forward locking portion provided at a forward end side of the metal terminal member and a rear locking portion provided at a rear end sides of the metal terminal member; the separator is composed of a forward separator and a rear separator which are disposed on forward and rear sides in the direction of the axial line, respectively, and are connected to each other, the forward separator including a first locking portion having a rearward-facing surface, the rear separator including a second locking portion having a forward-facing surface; and the metal terminal member is held between the forward separator and the rear separator such that the forward locking portion is in locking engagement with the rearward-facing surface and the rear locking portion is in locking engagement with the forward-facing surface.

According to this gas sensor, the forward locking portion and the rear locking portion of the metal terminal member to which the lead wire is connected are respectively brought into locking engagement with and held by the rearward-facing surface of the forward separator and the forward-facing surface of the rear separator. Therefore, it is possible to prevent the metal terminal member from coming off toward the forward side and the rear side within the forward separator and the rear separator.

As a result, the metal terminal member is reliably held within the forward separator and the rear separator, and the metal terminal member is prevented from moving in the axial direction due to, for example, application of external force or the like, whereby stable electrical connection can be established between the electrode pad of the sensor element and the above-mentioned metal terminal member.

Also, since the metal terminal member is held within the forward separator and the rear separator, it is unnecessary to excessively decrease the clearances between the metal terminal member and the wall surfaces of the insertion holes of these separators. Therefore, it is possible to prevent an increase in the rearward pulling-in load acting on the lead wire, which increase would otherwise occur due to an increase in the frictional force produced between the metal terminal member and the wall surfaces of the insertion holes. Thus, a decrease in the efficiency of assembling work can be prevented.

In the gas sensor of the present invention, a contact point at which the metal terminal member contacts the electrode pad may be located between the rearward-facing surface and the forward-facing surface.

According to this gas sensor, the metal terminal member is in locking engagement with the forward separator and the rear separator at two positions located on the front and rear sides of the contact point. Therefore, it is possible to more reliably prevent the metal terminal member, which is in contact with the electrode pad at the contact point, from moving in the axial direction, for example, due to application of external force or the like. Thus, the electrical connection between the metal terminal member and the electrode pad becomes more stable.

The gas sensor of the present invention may be such that the metal terminal member is composed of a forward metal terminal member and a rear metal terminal member which are disposed on the forward side and the rear side, respectively, and are connected to each other, the forward metal terminal member having the forward locking portion, the rear metal terminal member having the rear locking portion; the rear metal terminal member is connected to the lead wire and is at least partially accommodated in the rear separator; and the forward metal terminal member is in contact with the electrode pad and is at least partially accommodated in the forward separator.

According to this gas sensor, the forward metal terminal member which has an elastic portion for connection with the electrode pad and is therefore complex in shape can be separated from the rear metal terminal member which is connected to the lead wire and requires complex work such as a crimping step. Therefore, in the crimping step, it is merely required to handle the rear metal terminal member having a simple shape. Thus, productivity is improved.

The gas sensor of the present invention may be such that a forward end portion of the rear metal terminal member assumes the form of at least a portion of a circular column or a cylindrical tube, the forward metal terminal member has, at its rear end, a connection portion assuming the form of at least a portion of a cylindrical tube, and the forward end portion is fitted into the connection portion.

According to this gas sensor, the connection portion and the forward end portion are of rotational symmetry about the axis. Therefore, even though the rear metal terminal member and the forward metal terminal member are positionally deviated about the axis to some extent, the forward end portion can be fitted into the connection portion, whereby the rear metal terminal member and the forward metal terminal member can be easily and reliably connected to each other.

A gas sensor manufacturing method of the present invention is a method of manufacturing a gas sensor which includes a sensor element having a plate shape, extending in a direction of an axial line and having an electrode pad on an outer surface of a rear end portion thereof; a metal terminal member extending in the direction of the axial line and electrically connected to the electrode pad; a tubular separator which holds the metal terminal member and surrounds a rear end portion of the sensor element; and a lead wire connected to a rear end portion of the metal terminal member and extending rearward of the separator, the metal terminal member having a forward locking portion provided at forward end of the metal terminal member and a rear locking portion provided at a rear end sides of the metal terminal member, the separator being composed of a forward separator and a rear separator which are disposed on forward and rear sides in the direction of the axial line, respectively, and are connected to each other, the forward separator including a first locking portion having a rearward-facing surface, the rear separator including a second locking portion having a forward-facing surface, the method comprising a step of disposing the forward separator on the forward side of the metal terminal member and the rear separator on the the rear side of the metal terminal member and holding the metal terminal member between the forward separator and the rear separator such that the forward locking portion is in locking engagement with the rearward-facing surface and the rear locking portion is in locking engagement with the forward-facing surface.

This gas sensor manufacturing method can also prevent the metal terminal member from coming off toward the forward side and the rear side within the forward separator and the rear separator. As a result, the metal terminal member is reliably held within the forward separator and the rear separator, and the metal terminal member is prevented from moving in the axial direction due to, for example, application of external force or the like, whereby stable electrical connection can be established between the electrode pad of the sensor element and the above-mentioned metal terminal member. Also, since the metal terminal member is held within the forward separator and the rear separator, it is unnecessary to excessively decrease the clearances between the metal terminal member and the wall surfaces of the insertion holes of these separators. Therefore, it is possible to prevent an increase in the rearward pulling-in load acting on the lead wire, which increase would otherwise occur due to an increase in the frictional force produced between the metal terminal member and the wall surfaces of the insertion holes. Thus, a decrease in the efficiency of assembling work can be prevented.

Effect of the Invention

The present invention provides a gas sensor which can reliably hold metal terminal members within a separator and realizes stable electrical connection between the metal terminal members and electrode pads of a sensor element.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An embodiment of the present invention will next be described.

Figure 1:
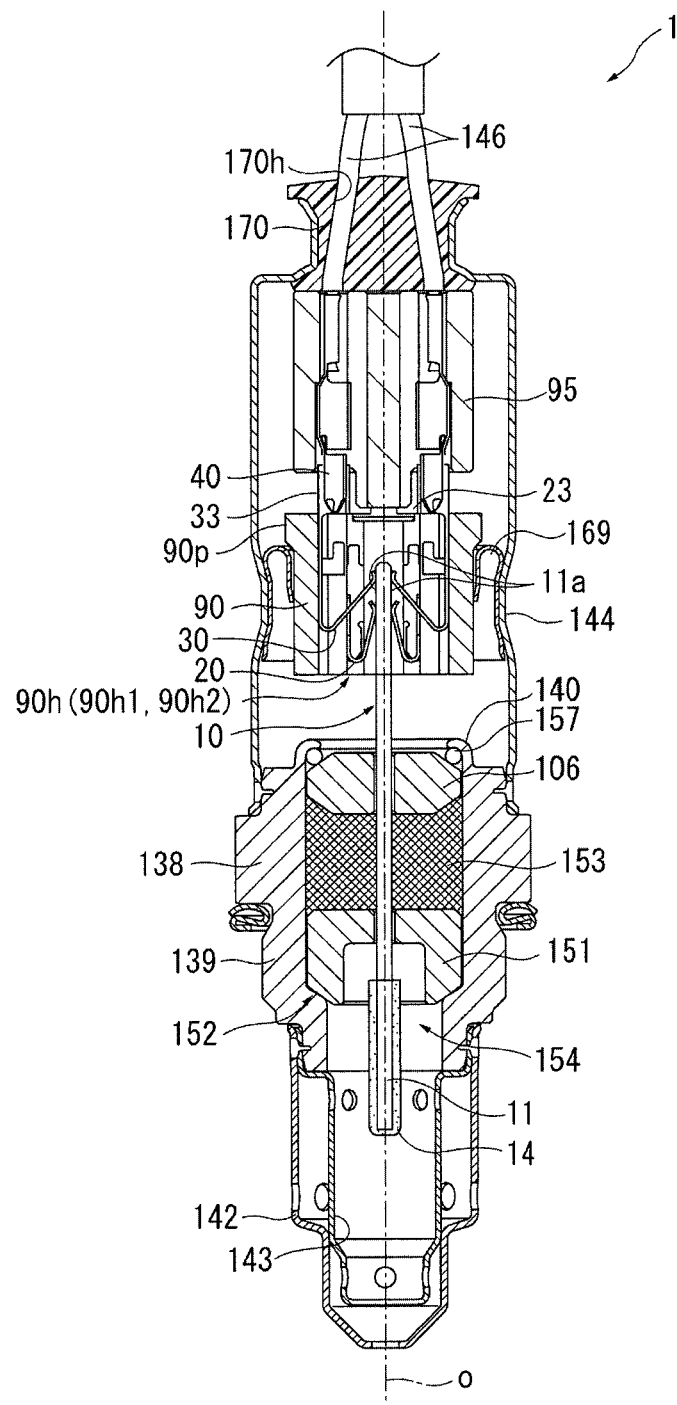
FIG. 1 is a sectional view of a gas sensor according to an embodiment of the present invention taken along an axial direction.
Figure 2:
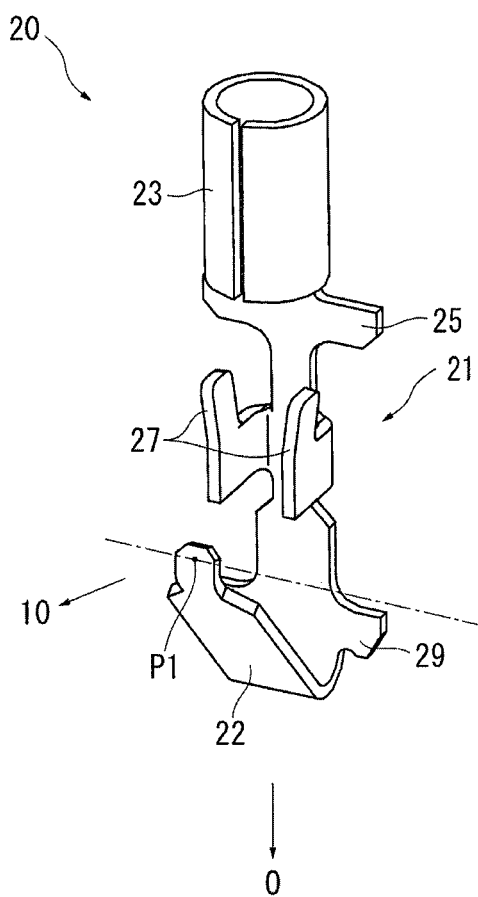
FIG. 2 is a perspective view of a forward metal terminal member.
Figure 3:
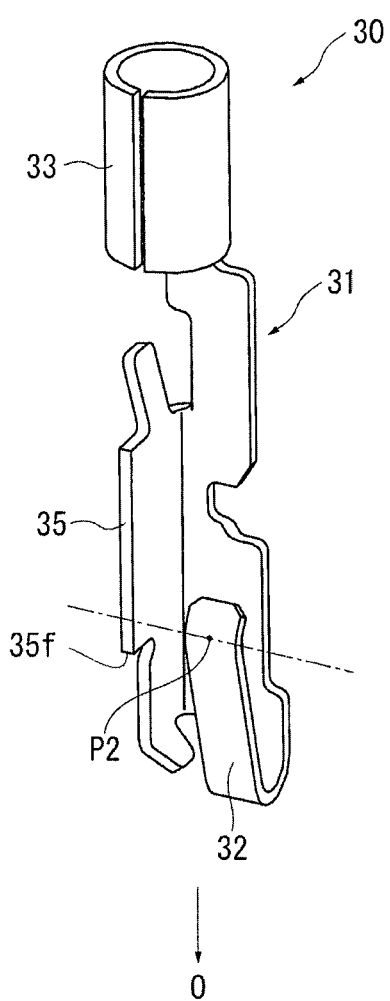
FIG. 3 is a perspective view of another forward metal terminal member.
Figure 4:
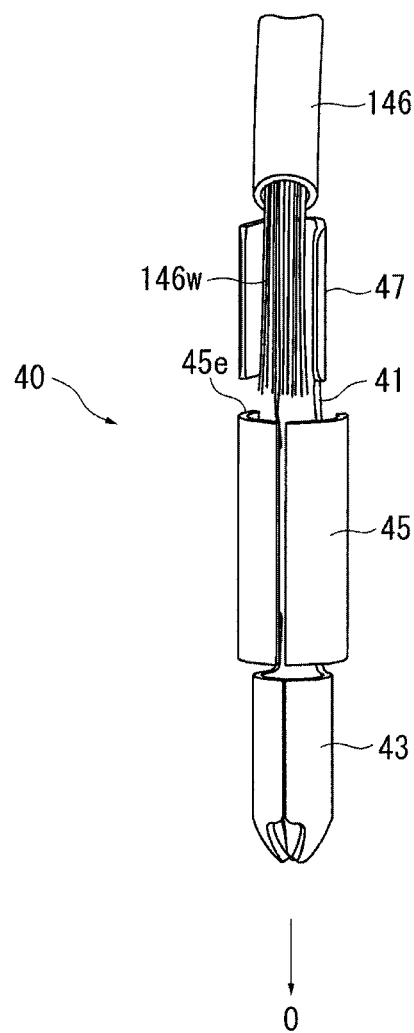
FIG. 4 is a perspective view of a rear metal terminal member.
Figure 5:
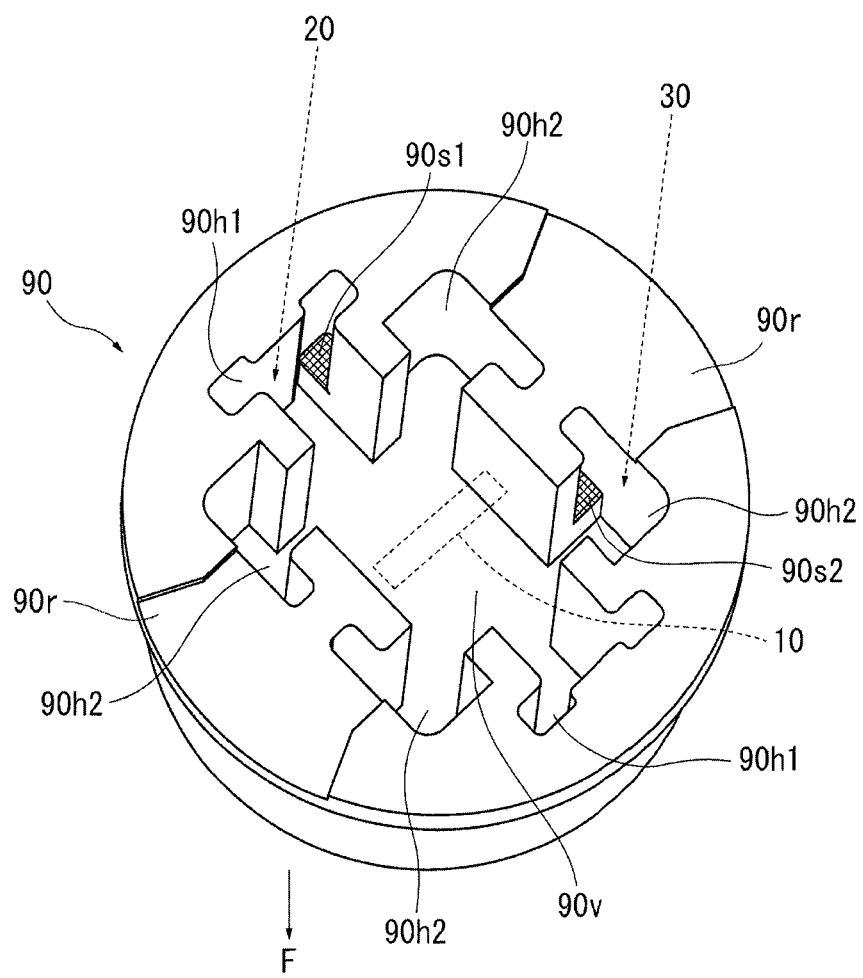
FIG. 5 is a perspective view of a forward separator.
Figure 6A:
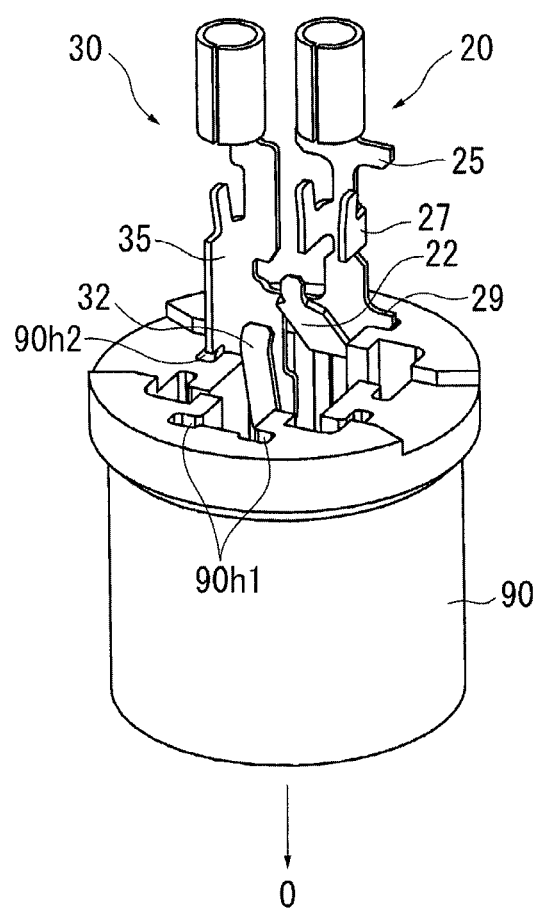
FIGS. 6A and 6B are views showing a step of fitting the forward metal terminal members into the forward separator.
Figure 6B:
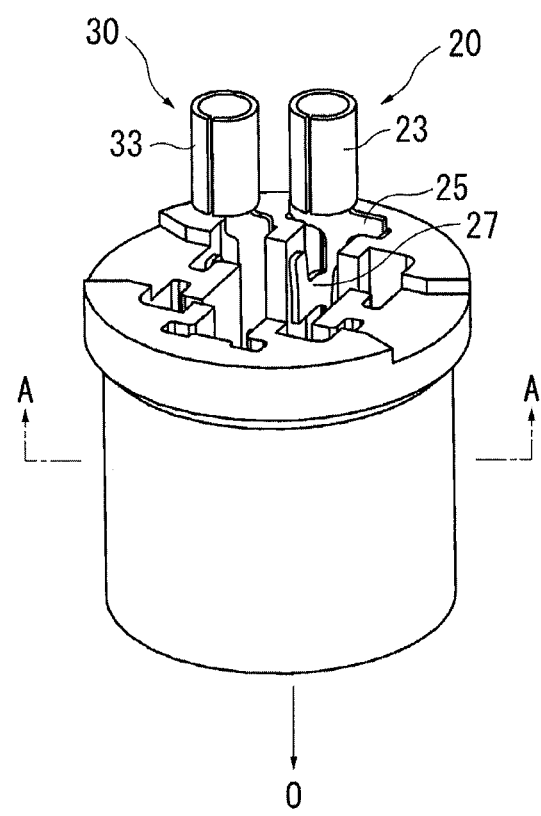
Figure 7:
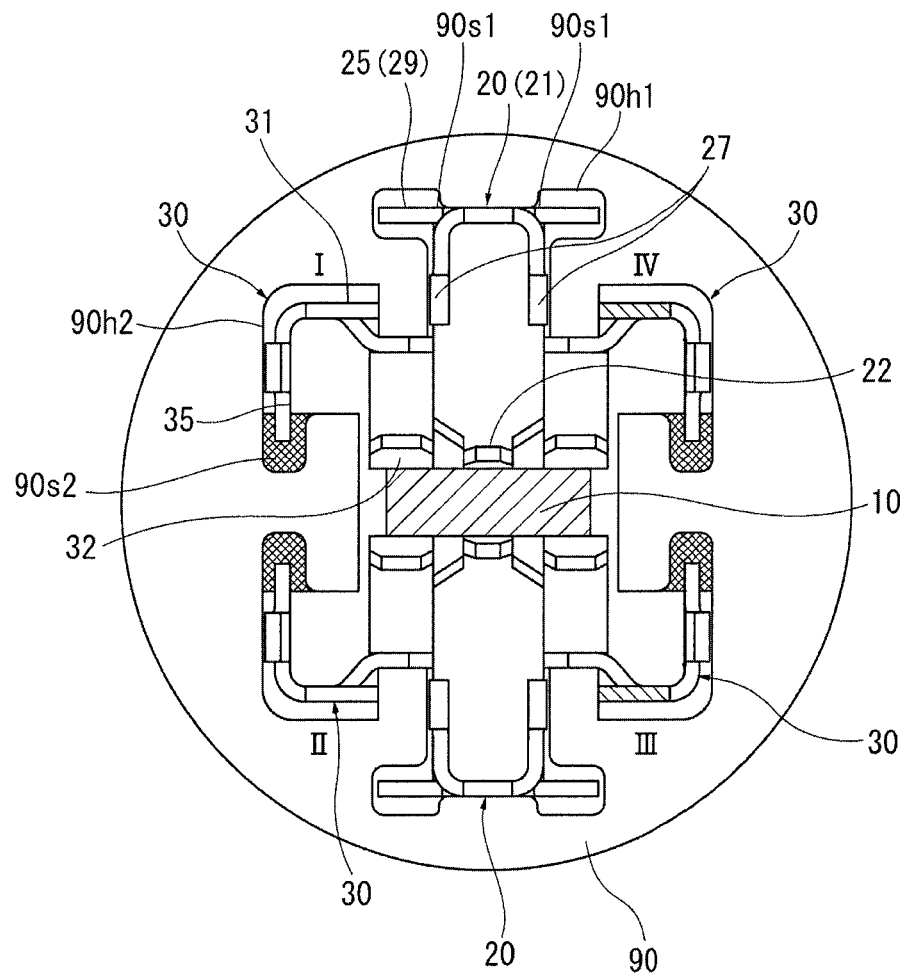
FIG. 7 is a sectional view showing a state in which the forward metal terminal members are held in the forward separator.
Figure 8A:
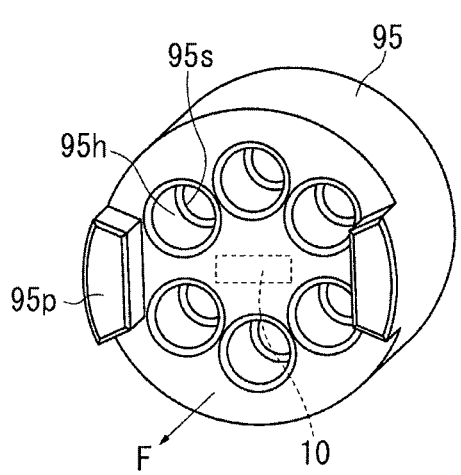
FIGS. 8A and 8B are views showing a step of fitting the rear metal terminal members into a rear separator.
Figure 8B:
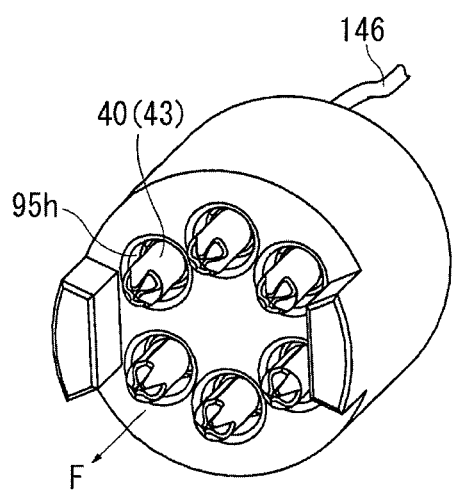

FIG. 1 is an overall sectional view of a gas sensor (NOx sensor) 1 according to an embodiment of the present invention taken along the direction of an axial line O; FIGS. 2 and 3 are perspective views of forward metal terminal members 20 and 30, respectively; FIG. 4 is a perspective view of a rear metal terminal member 40; FIG. 5 is a perspective view of a forward separator 90; FIGS. 6A and 6B are views showing a step of fitting the forward metal terminal members 20 and 30 into the forward separator 90; FIG. 7 is a sectional view showing a state in which the forward metal terminal members 20 and 30 are held in the forward separator 90; and FIGS. 8A and 8B are views showing a step of fitting the rear metal terminal members 40 into a rear separator 95. Notably, FIG. 7 shows a cross section taken along a line A-A of FIG. 6B and extending perpendicular to the direction of the axial line O.

The gas sensor 1 is an NOx sensor for detecting the concentration of oxygen in exhaust gas from automobiles and various internal combustion engines.

In FIG. 1, the gas sensor 1 includes a tubular metallic shell 138 having a threaded portion 139 formed on its outer surface and adapted for fixation to an exhaust pipe; a plate-like sensor element 10 extending in the direction of the axial line O (the longitudinal direction of the gas sensor 1, or the vertical direction in the drawing); a tubular ceramic sleeve 106 disposed in such a manner as to radially surround the sensor element 10; a tubular forward separator 90 made of ceramic and disposed in such a manner as to surround a rear end portion of the sensor element 10 inserted into a forward internal space thereof; six forward metal terminal members 20 and 30 (only four of them illustrated in FIG. 1) inserted into and held in insertion holes 90h (90h1 and 90h2) extending through the forward separator 90 in the direction of the axial line O; a tubular rear separator 95 made of ceramic; and six rear metal terminal members 40 (only two of them illustrated in FIG. 1) held in the rear separator 95.

As will be described later, the rear separator 95 is disposed on the rear side of and engaged with the forward separator 90.

The forward metal terminal members 20 and 30 and the rear metal terminal members 40 are disposed on the forward side and the rear side, respectively, and are mutually connected. A member formed by connecting the forward metal terminal member 20 (30) and the corresponding rear metal terminal member 40 may be referred to as the "metal terminal member."

As will be described in detail later, as shown in FIG. 5, the insertion holes 90h1 and 90h2 of the forward separator 90 communicate with the internal space 90v on the forward F side of the forward separator 90, and the forward metal terminal members 20 and 30 held in the insertion holes 90h1 and 90h2 face the outer surface of a rear end portion of the sensor element 10 and are electrically connected to respective electrode pads 11a formed on the outer surface.

Three electrode pads 11a are juxtaposed in the width direction of the sensor element 10 on each of opposite sides of the rear end portion of the sensor element 10. The electrode pads 11a can be formed of, for example, a sintered body which predominantly contains Pt.

Meanwhile, a forward-end gas detecting section 11 of the sensor element 10 is covered with a porous protection layer 14 of alumina or the like.

The metallic shell 138 is a generally tubular member formed of stainless steel and having a through hole 154 extending therethrough in the direction of the axial line and a ledge portion 152 protruding radially inward of the through hole 154. The sensor element 10 is disposed in the through hole 154 such that a forward end portion thereof protrudes from the forward end of the through hole 154. Further, the ledge portion 152 is tapered inward and inclined from a plane perpendicular to the direction of the axial line.

Within the through hole 154 of the metallic shell 138, a generally annular ceramic holder 151 made of alumina, a powder filler layer 153 (hereinafter, may be called the talc ring 153), and the above-mentioned ceramic sleeve 106 are stacked in this order from the forward side to the rear side in such a manner as to radially surround the sensor element 10.

Also, a crimp packing 157 is disposed between the ceramic sleeve 106 and a rear end portion 140 of the metallic shell 138. The rear end portion 140 of the metallic shell 138 is crimped in such a manner as to press the ceramic sleeve 106 forward through the crimp packing 157.

Meanwhile, as shown in FIG. 1, a dual protector made of metal (e.g., stainless steel) is attached, by welding or the like, to the outer circumference of a forward end portion (a lower portion in FIG. 1) of the metallic shell 138 and covers a protruding portion of the sensor element 10. The dual protector has a plurality of holes and consists of an outer protector 142 and an inner protector 143.

A sleeve 144 is fixed to the outer circumference of a rear end portion of the metallic shell 138. Lead wires 146 are connected to rear end portions of the rear metal terminal members 40, respectively, and extend rearward from the rear end of the rear separator 95.

A grommet 170 made of rubber is disposed in a rear-end (an upper-end in FIG. 1) opening portion of the sleeve 144 and has lead-wire insertion holes 170h into which six lead wires 146 (only two of them illustrated in FIG. 1) extending from the rear separator 95 are inserted respectively.

The forward separator 90 is disposed around a rear end portion (an upper end portion in FIG. 1) of the sensor element 10 protruding from the rear end portion 140 of the metallic shell 138 and has a collar portion 90p protruding radially outward from the outer surface thereof. The collar portion 90p is in contact with the sleeve 144 through a holding member 169, whereby the forward separator 90 is held within the sleeve 144.

The rear separator 95 is disposed between the grommet 170 and the forward separator 90, and elastic force of the grommet 170 causes the rear separator 95 to press forward the forward separator 90. As a result, the collar portion 90p is pressed against the holding member 169, whereby the forward separator 90 and the rear separator 95 are held within the sleeve 144 in a mutually connected condition (i.e., without separation in the direction of the axial line O).

FIGS. 2 and 3 are perspective views of the forward metal terminal members 20 and 30, respectively. The present embodiment uses forward metal terminal members of two types; specifically, the forward metal terminal members 20 and 30.

As shown in FIG. 7, since the four forward metal terminal members 30 are such that the forward metal terminal members 30 adjacent to each other in the forward separator 90 are axisymmetric in shape, one of the forward metal terminal members 30 (one located at upper left position I in FIG. 7) will be used for description.

The forward metal terminal member 30 located at lower left position II in FIG. 7 is axisymmetric to the forward metal terminal member 30 located at position I with respect to a line along a plane of the sensor element 10. The forward metal terminal member 30 located at lower right position III in FIG. 7 is axisymmetric to the forward metal terminal member 30 located at position II with respect to a line perpendicular to the plane of the sensor element 10. The forward metal terminal member 30 located at upper right position IV in FIG. 7 is axisymmetric to the forward metal terminal member 30 located at position I with respect to the line perpendicular to the plane of the sensor element 10.

The two forward metal terminal members 20 face each other in the forward separator 90 and are axisymmetric in shape; therefore, one of the forward metal terminal members 20 (one located at an upper position in FIG. 7) will be used for description.

The lower forward metal terminal member 20 in FIG. 7 is axisymmetric to the upper forward metal terminal member 20 with respect to the line along the plane of the sensor element 10. Each of the forward metal terminal members 20 is located between the two forward metal terminal members 30 with respect to the width direction of the sensor element 10.

As shown in FIG. 2, the forward metal terminal member 20 extends in the direction of the axial line O and integrally includes a connection portion 23 to be connected to the rear metal terminal member 40, a generally plate-like body portion 21 connected to the forward end of the connection portion 23, and an elastic portion 22 bent toward the sensor element 10 at the forward end of the body portion 21.

The forward metal terminal member 20 can be manufactured, for example, as follows: a blank is punched out from a single metal plate (INCONEL (registered trademark) or the like), and then the blank is bent to a predetermined shape. The manufacturing method is not limited thereto.

The connection portion 23 has a cylindrical tubular shape having a C-shaped section, and the rear metal terminal member 40 whose forward end portion has a cylindrical tubular shape having a C-shaped section is fitted into the connection portion 23. In this case, the forward metal terminal member 20 is indirectly connected to the lead wire 146 through the rear metal terminal member 40.

A portion of the body portion 21 at the center thereof with respect to the direction of the axial line O has wing portions on opposite sides with respect to the width direction thereof. The wing portions are bent 90 degrees toward the sensor element 10 side to thereby form a pair of holding portions 27 whose sections partially constitute a squarish-letter-U-shaped section. The connection portion 23 is integrally connected to the rear end of the body portion 21. The body portion 21 serves as a base portion of the forward metal terminal member 20 for securing strength of the forward metal terminal member 20. The two holding portions 27 fan out rearward.

Also, a rear end portion of the body portion 21 located on the rear side with respect to the direction of the axial line O has a pair of quadrangular rear holding portions 25 which are flush with the body portion 21 and extend outward from opposite sides of the rear end portion of the body portion 21 with respect to the width direction thereof. Similarly, a forward end portion of the body portion 21 located on the forward side with respect to the direction of the axial line O has a pair of quadrangular forward holding portions 29 which are flush with the body portion 21 and extend outward from opposite sides of the forward end portion of the body portion 21 with respect to the width direction thereof.

The pair of quadrangular forward holding portions 29 may be referred to as the "forward locking portion."

The elastic portion 22 is bent rearward and toward the sensor element 10 from the forward end of the body portion 21 and is elastically connected to the electrode pad 11a (see FIG. 1) at a contact P1. The elastic portion 22 elastically bends radially in relation to the body portion 21.

As shown in FIG. 3, the forward metal terminal member 30 extends in the direction of the axial line O and integrally includes a connection portion 33 to be connected to the rear metal terminal member 40, a generally plate-like body portion 31 connected to the forward end of the connection portion 33, and an elastic portion 32 bent toward the sensor element 10 at the forward end of the body portion 31.

The forward metal terminal member 30 can be manufactured, for example, as follows: a blank is punched out from a single metal plate (INCONEL (registered trademark) or the like), and then the blank is bent to a predetermined shape. The manufacturing method is not limited thereto.

Similar to the connection portion 23, the connection portion 33 has a cylindrical tubular shape, and the rear metal terminal member 40 is fitted into the connection portion 33.

The body portion 31 has an L-shaped section and has a wing portion on one side with respect to the width direction of the body portion 31. The wing portion is bent 90 degrees toward the sensor element 10 side to thereby form a position holding portion 35. The connection portion 33 is integrally connected to the rear end of the body portion 31. The body portion 31 serves as a base portion of the forward metal terminal member 30 for securing strength of the forward metal terminal member 30. Also, a portion of the position holding portion 35 located slightly forward of the center thereof with respect to the direction of the axial line O is recessed toward the body portion 31 to thereby form a stepped shape, and its forward-facing surface forms a forward end portion 35f.

The forward end portion 35f may be referred to as the "forward locking portion."

The elastic portion 32 is bent rearward and toward the sensor element 10 from the forward end of the body portion 31 and is elastically connected to the electrode pad 11a (see FIG. 1) at a contact P2. The elastic portion 32 elastically bends radially in relation to the body portion 31.

Meanwhile, as shown in FIG. 4, the rear metal terminal member 40 extends in the direction of the axial line O and integrally includes a crimp terminal portion 47, a generally plate-like neck portion 41, a cylindrical tubular large-diameter portion 45, and a cylindrical tubular forward end portion 43. The crimp terminal portion 47 is connected to the lead wire 146. The neck portion 41 is connected to the forward end of the crimp terminal portion 47. The large-diameter portion 45 is connected to the forward end of the neck portion 41 and is formed by bending a plate-like portion to have a C-shaped section. The forward end portion 43 is connected to the forward end of the large-diameter portion 45 and is formed by bending a plate-like portion to have a C-shaped section.

The rear metal terminal member 40 can be manufactured, for example, as follows: a blank is punched out from a single metal plate (SUS304 or the like), and then the blank is bent to a predetermined shape. The manufacturing method is not limited thereto.

The crimp terminal portion 47 crimps uncovered conductors 146w of a forward end portion of the lead wire 146 to thereby tubularly grip the conductors 146w.

The forward end portion 43 has a cylindrical tubular form and tapers off forward. The forward end portion 43 is fitted into the tubular connection portion 23 or 33, whereby the rear metal terminal member 40 is electrically connected to the forward metal terminal member 20 or 30.

The large-diameter portion 45 is greater in diameter than the crimp terminal portion 47 and the forward end portion 43, and a rearward-facing surface 45e of the large-diameter portion 45 is located radially outward of the crimp terminal portion 47.

The rearward-facing surface 45e may be referred to as the "rear locking portion."

As shown in FIG. 5, the forward separator 90 has the insertion holes 90h1 and 90h2, and the insertion holes 90h1 and 90h2 communicate with the internal space 90v on the forward F side of the forward separator 90.

The insertion holes 90h2 are disposed at four corners of the forward separator 90, and the insertion holes 90h1 are located between two insertion holes 90h2 along the width direction of the sensor element 10.

A rearward-facing surface 90s1 is formed on the forward side of the insertion holes 90h1, and a rearward-facing surface 90s2 is formed on the forward side of the insertion holes 90h2.

Each of the rearward-facing surfaces 90s1 and 90s2 may be referred to as the "first locking portion."

Notably, recesses 90r extending along the width direction of the sensor element are formed on the rearward-facing surface of the rear separator 90 to be located on opposite sides of the internal space 90v. As will be described in detail later, the bottoms of the recesses 90r come into engagement with protrusions 95p of the rear separator 95.

As shown in FIGS. 6A and 6B, when the forward metal terminal member 20 is inserted from the rear side into the insertion hole 90h1 (FIG. 6A), the forward holding portions 29 of the forward metal terminal member 20 butts against the rearward-facing surface 90s1 to thereby prevent coming off of the forward metal terminal member 20 toward the forward side. Thus, the forward metal terminal member 20 is held in the forward separator 90 (FIG. 6B).

Similarly, when the forward metal terminal member 30 is inserted from the rear side into the insertion hole 90h2 (FIG. 6A), the forward end portion 35f of the forward metal terminal member 30 butts against the rearward-facing surface 90s2 to thereby prevent coming off of the forward metal terminal member 30 toward the forward side. Thus, the forward metal terminal member 30 is held in the forward separator 90 (FIG. 6B).

In a state in which the forward metal terminal members 20 and 30 are held in the forward separator 90, the connection portions 23 and 33 protrude rearward from the forward separator 90 (FIG. 6B).

Meanwhile, as shown in FIGS. 8A and 8B, the rear separator 95 has six circumferentially disposed insertion holes 95h. Each of the insertion holes 95h is large in diameter on the forward F side and reduces in diameter stepwise in the vicinity of the center with respect to the direction of the axial line O, and the resultant stepped portion forms a forward-facing surface 95s (FIG. 8A).

The forward-facing surface 95s may be referred to as the "second locking portion."

Two protrusions 95p protruding in the direction of the axial line O are formed at the periphery of the forward end surface of the rear separator 95. The protrusions 95p are engaged with the bottoms of the recesses 90r of the forward separator 90.

The lead wire 146 is passed beforehand through the insertion hole 95h such that a distal end of the lead wire 146 appears on the forward side of the rear separator 95, and the distal end of the lead wire 146 is connected to the rear metal terminal member 40 on the forward side of the rear separator 95. Next, a portion of the rear metal terminal member 40 on the lead wire 146 side is inserted into the insertion hole 95h from the forward F side, and the lead wire 146 is pulled rearward. As a result, the rearward-facing surface 45e (see FIG. 4) of the large-diameter portion 45 of the rear metal terminal member 40 comes into contact with the forward-facing surface 95s to thereby prevent coming off of the rear metal terminal member 40 toward the rear side. Thus, the rear metal terminal member 40 is held in the rear separator 95 (FIG. 8B).

In this state, a forward portion of the forward end portion 43 (a portion of the forward end portion 43 located forward of the center with respect to the direction of the axial line O) of the rear metal terminal member 40 protrudes from the forward end surface of the rear separator 95.

The outer diameter of the large-diameter portion 45 is slightly smaller than the inner diameter of the insertion hole 95h. The large-diameter portion 45 comes into engagement with the wall surface of the insertion hole 95h to thereby hold the rear metal terminal member 40 within the rear separator 95.

Next, with reference to FIGS. 9A and 9B, FIGS. 10A and 10B, FIGS. 11A and 11B, and FIGS. 12A and 12B, there will be described a method of holding the forward metal terminal members 20 and 30 and the rear metal terminal members 40 by the forward separator 90 and the rear separator 95 such that the forward metal terminal members 20 and 30 and the rear metal terminal members 40 are sandwiched in the direction of the axial line O between the forward separator 90 and the rear separator 95.

Since the forward metal terminal members 20 and 30 and the rear metal terminal members 40 corresponding thereto are inserted into different insertion holes of the separators 90 and 95, the cross sections of the separators 90 and 95 including their insertion holes are shown in FIGS. 9A and 9B and FIGS. 10A and 10B.

Figure 9A:
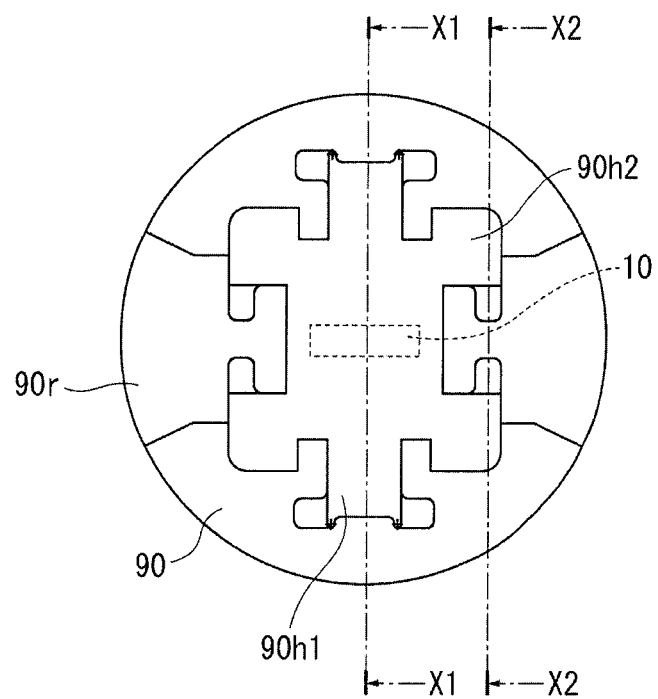
FIGS. 9A and 9B are sectional views of the forward separator including insertion holes thereof.
Figure 9B:
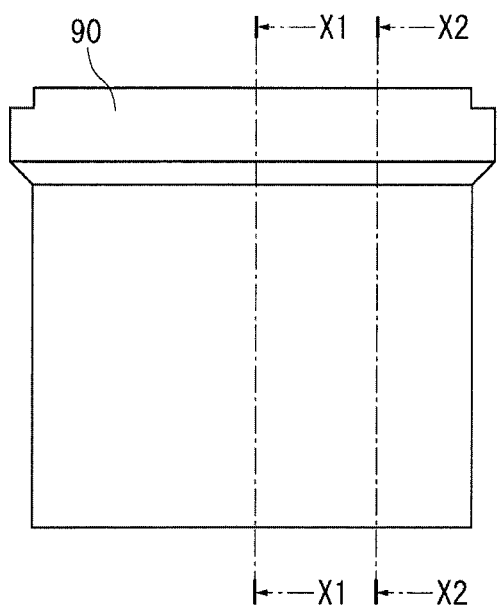

As shown in FIGS. 9A and 9B, a cross section of the forward separator 90 which is perpendicular to the plate surface of the sensor element 10, passes through the opposite insertion holes 90$h$1, and extends along the direction of the axial line O is represented by a line X1-X1. Also, a cross section of the forward separator 90 which is perpendicular to the plate surface of the sensor element 10, passes through the opposite insertion holes 90$h$2, and extends along the direction of the axial line O is represented by a line X2-X2.

Figure 10A:
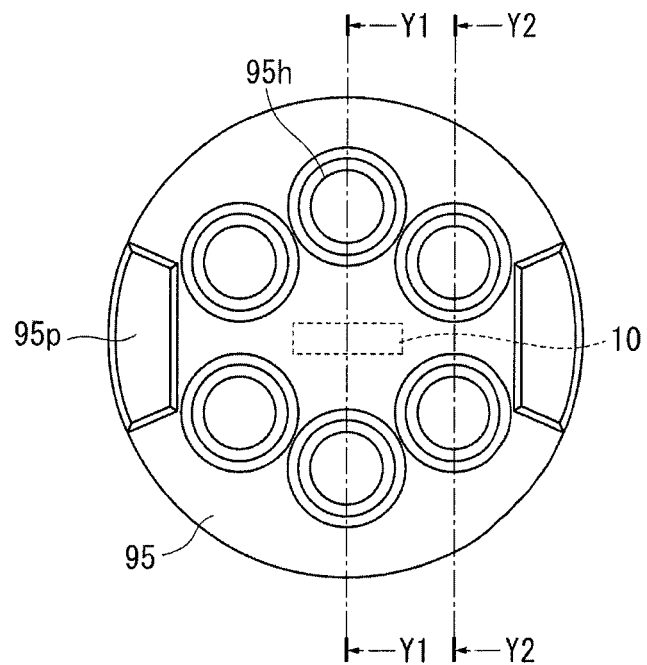
FIGS. 10A and 10B are sectional views of the rear separator including insertion holes thereof.
Figure 10B:
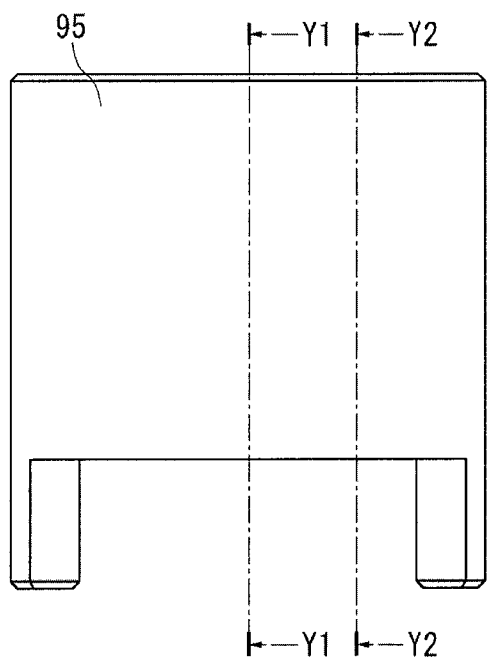

Similarly, as shown in FIGS. 10A and 10B, a cross section of the rear separator 95 which extends along the line X1-X1 is represented by a line Y1-Y1, and a cross section of the rear separator 95 which extends along the line X2-X2 is represented by a line Y2-Y2.

Figure 11A:
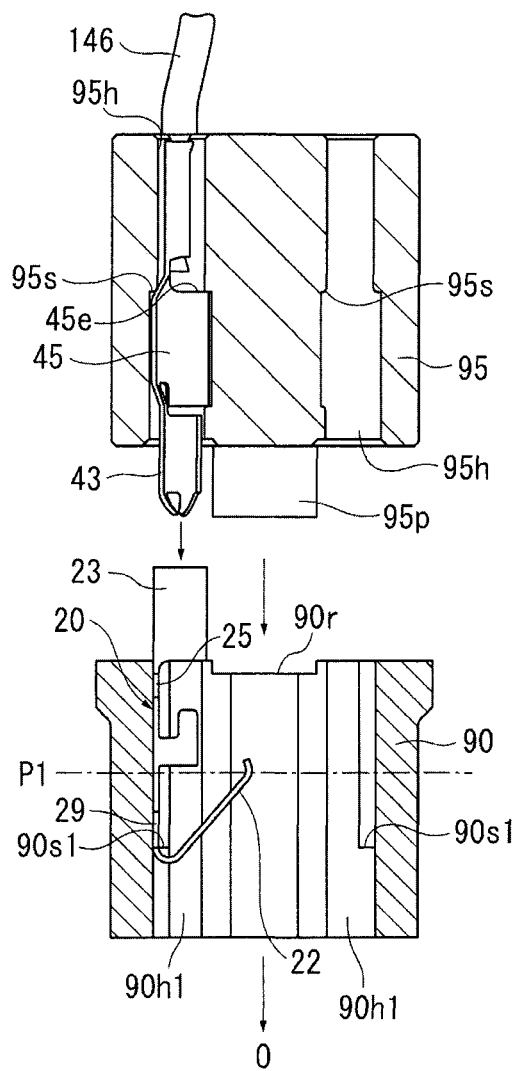
FIGS. 11A and 11B are views showing a step of combining the forward separator and the rear separator, the views being sectional views taken along a predetermined cross section shown in FIGS. 9A and 9B and FIGS. 10A and 10B.
Figure 11B:
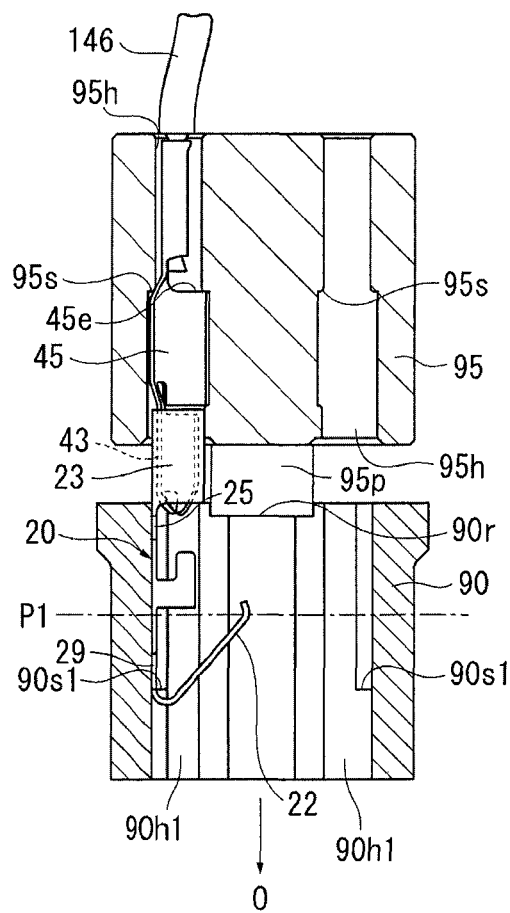

FIGS. 11A and 11B are views showing a step of combining the forward separator 90 and the rear separator 95, in which the forward separator 90 is shown in the cross section along the line X1-X1 in FIGS. 9A and 9B and the rear separator 95 is shown in the cross section along the line Y1-Y1 in FIGS. 10A and 10B.

As shown in FIGS. 11A and 11B, the forward holding portion (forward locking portion) 29 of the forward metal terminal member 20 is in locking engagement with the rearward-facing surface (first locking portion) 90$s$1. Also, the rearward-facing surface (forward locking portion) 45$e$ of the corresponding rear metal terminal member 40 is engaged with the forward-facing surface (second locking portion) 95$s$ (FIG. 11A).

In this state, the protrusions 95$p$ of the rear separator 95 are brought into engagement with the bottoms of the recesses 90$r$ of the forward separator 90 in the direction of the axial line O, and the forward separator 90 and the rear separator 95 are sandwiched and held between the holding member 169 and the grommet 170 which are not shown in FIGS. 11A and 11B, whereby the forward separator 90 and the rear separator 95 are connected to each other (FIG. 11B).

At that time, the forward end portion 43 of the rear metal terminal member 40 projecting toward the forward side of the rear separator 95 is fitted into the connection portion 23 of the forward metal terminal member 20 projecting toward the rear side of the forward separator 90, whereby the two metal terminal members are connected together.

In the state in which the two metal terminal members are connected together, the forward holding portion 29 is brought into locking engagement with the rearward-facing surface 90$s$1, whereby coming off of the forward metal terminal member 20 toward the forward side is prevented. Similarly, the rearward-facing surface 45$e$ is brought into locking engagement with the forward-facing surface 95$s$, whereby coming off of the rear metal terminal member 40 toward the rear side is prevented. Since the forward metal terminal member 20 and the rear metal terminal member 40 are connected in the direction of the axial line O to thereby form an integral "metal terminal member," it is possible to prevent the forward metal terminal member 20 and the rear metal terminal member 40 from coming off toward the forward side and the rear side within the forward separator 90 and the rear separator 95.

Figure 12A:
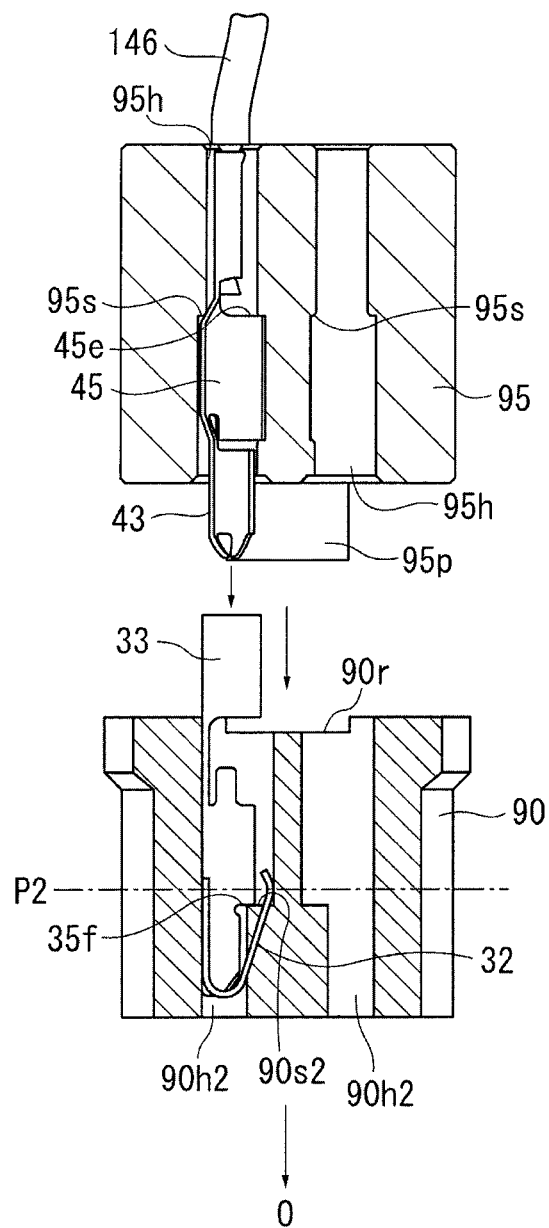
FIGS. 12A and 12B are views showing the step of combining the forward separator and the rear separator, the views being sectional views taken along a different cross section shown in FIGS. 9A and 9B and FIGS. 10A and 10B.
Figure 12B:
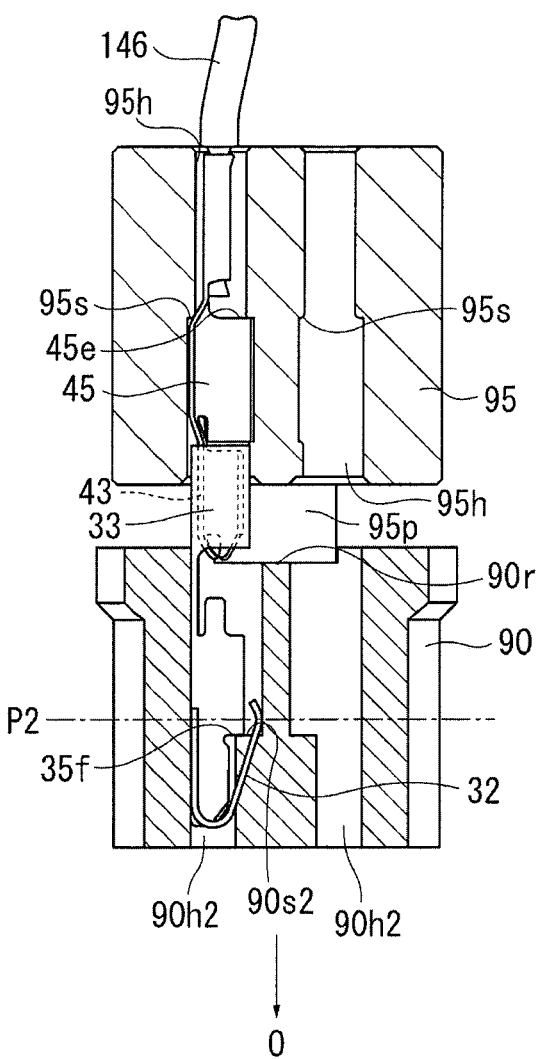

FIGS. 12A and 12B are views showing the step of combining the forward separator 90 and the rear separator 95, in which the forward separator 90 is shown in the cross section along the line X2-X2 in FIGS. 9A and 9B and the rear separator 95 is shown in the cross section along the line Y2-Y2 in FIGS. 10A and 10B.

As shown in FIGS. 12A and 12B, the forward end portion (forward locking portion) 35$f$ of the forward metal terminal member 30 is in locking engagement with the rearward-facing surface (first locking portion) 90$s$2. Also, the rearward-facing surface (forward locking portion) 45$e$ of the corresponding rear metal terminal member 40 is in locking engagement with the forward-facing surface (second locking portion) 95$s$ (FIG. 12A).

In this state, the protrusions 95$p$ of the rear separator 95 are brought into engagement with the bottoms of the recesses 90$r$ of the forward separator 90 in the direction of the axial line O, and the forward separator 90 and the rear separator 95 are sandwiched and held between the holding member 169 and the grommet 170 which are not shown in FIGS. 12A and 12B, whereby the forward separator 90 and the rear separator 95 are connected to each other (FIG. 12B).

At that time, the forward end portion 43 of the rear metal terminal member 40 projecting toward the forward side of the rear separator 95 is connected to the connection portion 33 of the forward metal terminal member 30 projecting toward the rear side of the forward separator 90, whereby the two metal terminal members are connected together.

In the state in which the two metal terminal members are connected together, the forward end portion 35$f$ is brought into locking engagement with the rearward-facing surface 90$s$2, whereby coming off of the forward metal terminal member 30 toward the forward side is prevented. Similarly, the rearward-facing surface 45$e$ is brought into locking engagement with the forward-facing surface 95$s$, whereby coming off of the rear metal terminal member 40 toward the rear side is prevented. Since the forward metal terminal member 30 and the rear metal terminal member 40 are connected in the direction of the axial line O to thereby form an integral "metal terminal member," it is possible to prevent the forward metal terminal member 30 and the rear metal terminal member 40 from coming off toward the forward side and the rear side within the forward separator 90 and the rear separator 95.

Notably, in FIGS. 11A, 11B, 12A, and 12B, in order to facilitate the understanding, one of two metal terminal members (the forward metal terminal members 20 (30) or the rear metal terminal members 40) located on opposite sides within the separator (the forward separator 90 and the rear separator 95) is omitted.

As a result of the above-described assembling work, the metal terminal members (the forward metal terminal members 20 and 30 and the rear metal terminal members 40) can be reliably held within the separator (the forward separator 90 and the rear separator 95). Therefore, the metal terminal members 20 and 30 are prevented from moving in the direction of the axial line O due to, for example, application of external force or the like, whereby the above-described metal terminal members can be electrically connected to the electrode pads 11$a$ of the sensor element 10 in a stable condition.

Also, it is unnecessary to hold the metal terminal members (the forward metal terminal members 20 and 30 and the rear metal terminal members 40) by excessively decreasing the clearances between the metal terminal members and the wall surfaces of the insertion holes 90$h$1, 90$h$2, and 95$h$ of the separator (the forward separator 90 and the rear separator 95). Therefore, it is possible to prevent an increase in the rearward pulling-in load acting on the lead wire 146, which increase would otherwise occur due to an increase in the frictional force produced between the metal terminal members and the wall surfaces of the insertion holes 90h1, 90h2, and 95h. Thus, a decrease in the efficiency of assembling work can be prevented.

Notably, in the present embodiment, as shown in FIGS. 11A and 11B, the contact point P1 between the forward metal terminal member 20 and the electrode pad 11a is located between the rearward-facing surface 90s1 (the first locking portion) and the forward-facing surface (the second locking portion) 95s along the direction of the axial line O. Similarly, as shown in FIGS. 12A and 12B, the contact point P2 between the forward metal terminal member 30 and the electrode pad 11a is located between the rearward-facing surface 90s2 (the first locking portion) and the forward-facing surface (the second locking portion) 95s along the direction of the axial line O.

As a result, the metal terminal members (the forward metal terminal members 20 and 30 and the rear metal terminal members 40) are brought into locking engagement with the separator (the forward separator 90 and the rear separator 95) at two positions located on the front and rear sides of the contact points P1 and P2. Therefore, for example, it is possible to more reliably prevent the metal terminal members 20 and 30, which are in contact with the electrode pads 11a at the contact points P1 and P2, from moving in the direction of the axial line O, for example, due to application of external force or the like. Thus, the electrical connection between the metal terminal members 20 and 30 and the electrode pads 11a becomes more stable.

In the present embodiment, as described above, two metal terminal members (i.e., the forward metal terminal member 20 connected to the electrode pad 11a of the sensor element 10 and the rear metal terminal member 40 connected to the lead wire 146) are connected as metal terminal members.

As a result, the forward metal terminal member 20 (30) which has an elastic portion for connection with the electrode pad 11a and is therefore complex in shape can be separated from the rear metal terminal member 40 which is connected to the lead wire 146 and requires complex work such as a crimping step. Therefore, in the crimping step, it is merely required to handle the rear metal terminal member 40 having a simple shape. Thus, productivity is improved.

Also, in the present embodiment, as shown in FIGS. 2 to 4, the forward end portion 43 of the rear metal terminal member 40 has a cylindrical tubular shape, and rear portions of the forward metal terminal members 20 and 30 form the cylindrical tubular connection portions 23 and 33.

As mentioned above, since the connection portions 23 and 33 and the forward end portion 43 are of rotational symmetry about the axial line O, even though the rear metal terminal member 40 and the forward metal terminal member 20 or 30 are positionally deviated about the axial line O to some extent, the forward end portion 43 can be fitted into the connection portion 23 or 33, whereby the rear metal terminal member 40 and the forward metal terminal member 20 or 30 can be easily and reliably connected to each other.

The present invention is not limited to the above embodiment, but extends into various modifications and equivalents encompassed by the ideas and scope of the invention.

Figure 13:
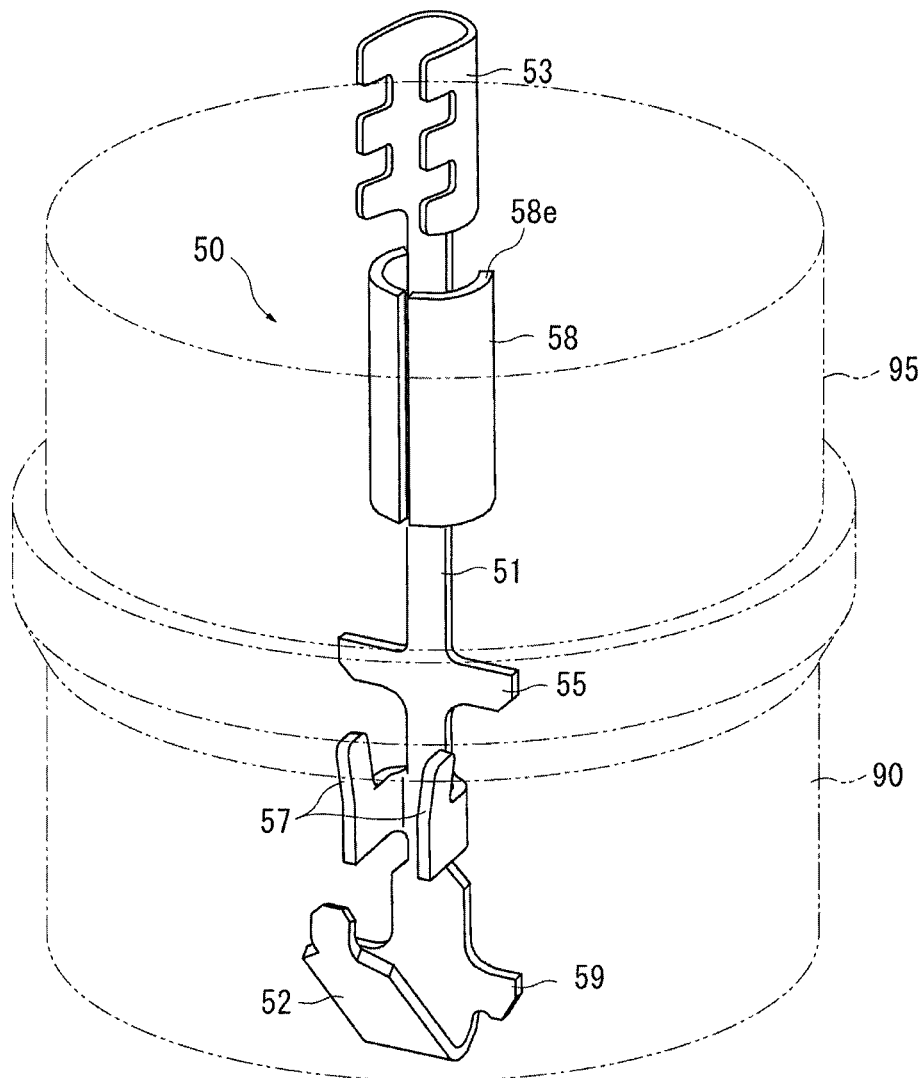
FIG. 13 is a perspective view showing a modification of the metal terminal member.
Figure 14:
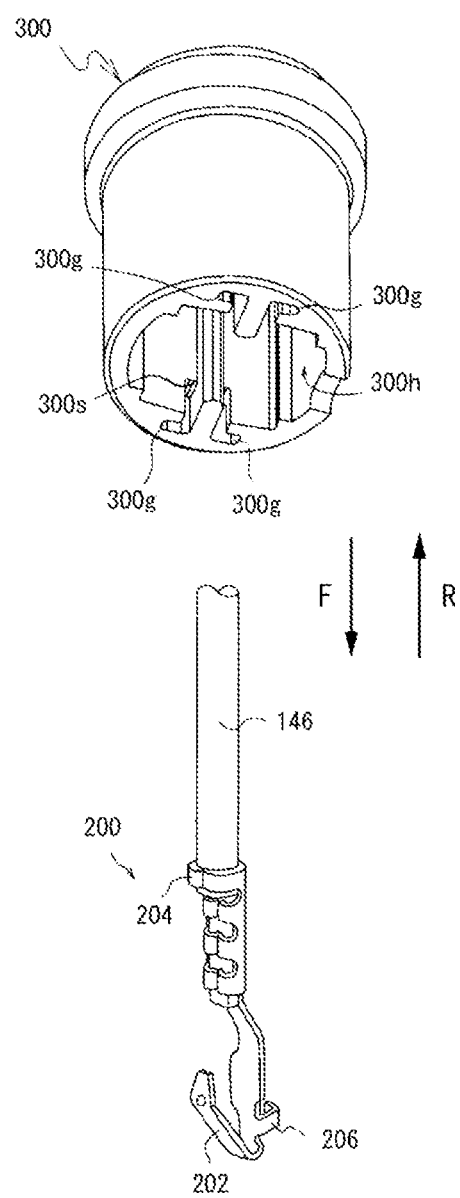
FIG. 14 is a perspective view a conventional metal terminal member.

For example, as shown in FIG. 13, a metal terminal member 50 may be formed as a single-piece member without dividing the metal terminal member 50 into forward and rear portions. In this case, a forward portion of the metal terminal member 50 has the same shape as the above-mentioned metal terminal member 20 with the connection portion 23 removed therefrom, and has a body portion 51, an elastic portion 52, rear holding portions 55, holding portions 57, and forward holding portions 59 which are identical in shape with the body portion 21, the elastic portion 22, the rear holding portions 25, the holding portions 27, and the forward holding portions 29, respectively.

Similarly, a rear portion of the metal terminal member 50 has the same shape as the above-mentioned metal terminal member 40 with the forward end portion 43 removed therefrom, and has a crimp terminal portion 53 and a large-diameter portion 58 which are identical in shape with the crimp terminal portion 47 and the large-diameter portion 45, respectively. A portion of the metal terminal member 50 on the forward side of the large-diameter portion 58 is integrally connected to the body portion 51.

In this metal terminal member 50, the forward holding portion 59 corresponds to the "forward locking portion" and the rearward-facing surface 58e of the large-diameter portion 58 corresponds to the "rear locking portion."

The metal terminal member and the separator are not limited in shape, etc., to those of the above embodiment.

The connection (coupling) structure between the rear metal terminal member and the forward metal terminal member is not limited to the above, but may be, for example, as follows: a rear end portion of the forward metal terminal member may have the shape of a male pin, and the male pin may be fitted into a tubular forward end portion of the rear metal terminal member.

In the case where a rear end portion of the forward metal terminal member and a forward end portion of the rear metal terminal member assume a tubular form, the tubular form is not limited to a cylindrical tube, but may be a prismatic tube such as a square tube. The tubular form may not be a completely closed tube, but may be at least a portion of a tube (may have a C-shaped section, for example). The tube of the forward metal terminal member or the rear metal terminal member may be replaced with a circular column or a portion of the circular column.

Examples of the gas sensor include, in addition to an NOx sensor, an oxygen sensor and a full range gas sensor.

DESCRIPTION OF REFERENCE NUMERALS

1: gas sensor
10: sensor element
11a: electrode pad
20, 30, 40, 50: metal terminal member
20, 30: forward metal terminal member
23, 33: connection portion
29, 35f, 59: forward locking portion
40: rear metal terminal member
43: forward end portion of rear metal terminal member
45e, 58e: rear locking portion
90: separator (forward separator)
90s1, 90s2: first locking portion (rearward-facing surface)
95: separator (rear separator)
95s: second locking portion (forward-facing surface)
146: lead wire
O: axial line
P1, P2: contact point

The invention claimed is:
1. A gas sensor comprising:
a sensor element having a plate shape, extending in a direction of an axial line and having an electrode pad on an outer surface of a rear end portion thereof;

a metal terminal member extending in the direction of the axial line and electrically connected to the electrode pad;

a tubular separator which holds the metal terminal member and surrounds the rear end portion of the sensor element; and a lead wire connected to a rear end portion of the metal terminal member and extending rearward of the separator, wherein the metal terminal member has a forward locking portion provided at a forward end side of the metal terminal member and a rear locking portion provided at a rear end side of the metal terminal member, the separator is composed of a forward separator and a rear separator which are disposed on forward and rear sides in the direction of the axial line, respectively, and are connected to each other, the forward separator including a first locking portion having a rearward-facing surface, the rear separator including a second locking portion having a forward-facing surface, and the metal terminal member is held between the forward separator and the rear separator such that the forward locking portion is in locking engagement with the rearward-facing surface and the rear locking portion is in locking engagement with the forward-facing surface.

2. The gas sensor according to claim 1, wherein a contact point, at which the metal terminal member contacts the electrode pad, is located between the rearward-facing surface and the forward-facing surface.

3. The gas sensor according to claim 2, wherein the metal terminal member is composed of a forward metal terminal member and a rear metal terminal member which are disposed on the forward side and the rear side, respectively, and are connected to each other, the forward metal terminal member having the forward locking portion, the rear metal terminal member having the rear locking portion, the rear metal terminal member is connected to the lead wire and is at least partially accommodated in the rear separator, and the forward metal terminal member is in contact with the electrode pad and is at least partially accommodated in the forward separator.

4. The gas sensor according to claim 1, wherein the metal terminal member is composed of a forward metal terminal member and a rear metal terminal member which are disposed on the forward side and the rear side, respectively, and are connected to each other, the forward metal terminal member having the forward locking portion, the rear metal terminal member having the rear locking portion, the rear metal terminal member is connected to the lead wire and is at least partially accommodated in the rear separator, and the forward metal terminal member is in contact with the electrode pad and is at least partially accommodated in the forward separator.

5. The gas sensor according to claim 4, wherein a forward end portion of the rear metal terminal member assumes the form of at least a portion of a circular column or a cylindrical tube, the forward metal terminal member has, at its rear end, a connection portion assuming the form of at least a portion of a cylindrical tube, and the forward end portion is fitted into the connection portion.

6. A method of manufacturing a gas sensor which includes:

a sensor element having a plate shape, extending in a direction of an axial line and having an electrode pad on an outer surface of a rear end portion thereof;

a metal terminal member extending in the direction of the axial line and electrically connected to the electrode pad;

a tubular separator which holds the metal terminal member and surrounds the rear end portion of the sensor element; and a lead wire connected to a rear end portion of the metal terminal member and extending rearward of the separator, wherein the metal terminal member having a forward locking portion provided at forward end of the metal terminal member and a rear locking portion provided at a rear end of the metal terminal member, the separator being composed of a forward separator and a rear separator which are disposed on forward and rear sides in the direction of the axial line, respectively, and are connected to each other, the forward separator including a first locking portion having a rearward-facing surface, the rear separator including a second locking portion having a forward-facing surface, the method comprising the steps of:

disposing the forward separator on the forward side of the metal terminal member and the rear separator on the rear side of the metal terminal member; and holding the metal terminal member between the forward separator and the rear separator such that the forward locking portion is in locking engagement with the rearward-facing surface and the rear locking portion is in locking engagement with the forward-facing surface.

* * * * *